United States Patent [19]

Nowinski et al.

[11] Patent Number: 4,609,707

[45] Date of Patent: * Sep. 2, 1986

[54] SYNTHESIS OF POLYMERS CONTAINING INTEGRAL ANTIBODIES

[75] Inventors: Robert C. Nowinski; Allan S. Hoffman, both of King County, Wash.

[73] Assignee: Genetic Systems Corporation, Seattle, Wash.

[ * ] Notice: The portion of the term of this patent subsequent to Apr. 16, 2002 has been disclaimed.

[21] Appl. No.: 668,248

[22] Filed: Nov. 7, 1984

Related U.S. Application Data

[63] Continuation-in-part of Ser. No. 550,929, Nov. 10, 1983, Pat. No. 4,511,478, and a continuation-in-part of Ser. No. 600,838, Apr. 16, 1984, abandoned.

[51] Int. Cl.[4] .......................... C08L 89/00; C08H 1/00
[52] U.S. Cl. ................................ 525/54.1; 526/238.1; 436/531; 436/535; 436/541; 436/543; 436/827; 210/692; 530/405; 530/817
[58] Field of Search .......................... 525/54.1, 54.11; 526/238.1; 260/112 R, 112 B, 112 T, 112.5 R; 210/692; 436/518, 531, 535, 536, 541, 543, 817, 819, 827

[56] References Cited

U.S. PATENT DOCUMENTS 2,853,457 9/1958 Gates, Jr. et al. ................ 526/238.1
3,969,287 7/1976 Jaworek et al. ................... 526/238.1

Primary Examiner—John Kight
Assistant Examiner—Nathan M. Nutter
Attorney, Agent, or Firm—Bertram I. Rowland

[57] ABSTRACT

A method is disclosed for the de novo synthesis of antibody-containing polymers and the preparation of a class of polymerizable compounds used in the synthesis of such antibody-containing polymers. Antibody-containing polymers formed from monomer/antibody conjugates and nonderivatized polymerizable compounds can be varied in formation of the polymer to provide control of (a) molecular spacing, steric accessibility and the number of antibody molecules that are integrally incorporated into the polymer backbone, and (b) the chemical and physical structure of the polymer itself, thus enabling specific tailoring of antibody-containing polymers for particular end-use application. Also disclosed is a method for the selective removal of a compound from a solution or suspension thereof using monomer/receptor conjugates where the compound has the capacity to bind to the receptor in the conjugate. The bound compound is removed by polymerization - induced separation of the monomer/receptor--compound complex from solution.

26 Claims, 3 Drawing Figures

SYNTHESIS OF POLYMERS CONTAINING INTEGRAL ANTIBODIES

CROSS-REFERENCE TO RELATED APPLICATION

This application is a continuation-in-part application of Ser. No. 550,929, filed Nov. 10, 1983, now U.S. Pat. No. 4,511,478, and continuation-in-part application Ser. No. 600,838, filed Apr. 16, 1984, now abandoned.

TECHNICAL FILED

The present invention relates to the de novo synthesis of polymers containing antibodies as an integral part of their backbone structure from monomer/antibody conjugates, and to selective removal of substances from solution by means of polymerization of monomer/receptor conjugates.

BACKGROUND ART

Polymerization of monomers or oligomers to form larger polymeric molecular structures (polymers), or the initiation of copolymerization of monomers with polymerizable polyunsaturated compounds is fundamental to polymer chemistry. Polymers may be formed from a single monomeric species (homopolymers), from a mixture of different monomers (copolymers), from polymerizable polyunsaturated compounds containing olefinic or acetylenic unsaturation, or from a mixture of polymerizable polyunsaturated compounds and one or more monomers. Linear, branched or cross-linked polymeric structures are possible. By varying the chemical composition and/or ratios of the monomer and/or polyunsaturated compound, it is possible to form either water-soluble or water-insoluble polymers which have a broad range of chemical and physical-properties. For example, water-soluble monomers (such as acrylamide) may be homopolymerized to form water-soluble homopolymers. Such monomers may also be copolymerized with less water-soluble monomers (such as N-alkyl or N,N-dialkyl acrylamides) or with cross-linking monomers (such as N,N'-methylenebisbisacrylamide) to form water-insoluble copolymers. Some water-soluble monomers (such as hydroxyethyl methacrylate or acrylonitrile) may be homopolymerized to form water-insoluble homopolymers.

Water-insoluble polymers (such as polysaccharides and polyacrylics) have been commonly used in the fields of biochemistry and immunology (affinity chromatography and immunoassays) as solid-phase supports with passively adsorbed or covalently linked antibodies. To date, however, antibodies have only been immobilized on preformed insoluble polymeric materials. For example, antibodies can be covalently bonded to cyanogen bromide-activated beads of Sepharose ® 4B (Pharmacia Fine Chemicals AB, Uppsala, Sweden), or beads of cross-linked acrylic polymers (U.S. Pat. No. 3,957,741). Also see *Affinity Chromatography and Related Techniques*, Proceedings of the Fourth International Symposium, Veldhoven, The Netherlands, June 22-26, 1981, eds. T. C. J. Gribnau, J. Visser, and R. C. F. Nivard, Elsevier Scientific Publishing Co., N.Y., 1982. The immobilized antibodies can then be used to specifically bind antigens to the solid surface of the beads followed by extensive washing to remove other adsorbed substances. Subsequently, the bound antigens can be eluted from the antibody-polymer matrix by treatment with chaotropic agents, high salt, or low-pH buffers. Antibodies have also been confined within capsule membranes for use in affinity chromatography (U.S. Pat. No. 4,257,884).

U.S. Pat. Nos. 3,314,905 and 3,453,222 disclose reaction products of proteinaceous materials and certain esters to form substances which are capable of polymerization (modified proteins). The reaction conditions under which these modified proteins are synthesized are harsh, e.g., elevated temperatures (typically 50° C.) and high pH (typically >8). The end products have use as resinprotein wood adhesives or flocculating agents.

U.S. Pat. No. 2,548,520 discloses high molecular weight materials prepared by copolymerizing proteins having unsaturated radicals chemically united therewith with unsaturated polymerizable monomers or their partial polymerization products. Production of these high molecular weight materials generally requires temperatures up to 100° C. Such high temperatures are not well tolerated be most proteins; thus the methods described are unsuitable for producing polymers of biologically active molecules.

U.S. Pat. No. 3,969,287 discloses a method for the preparation of carrier-bound proteins, wherein the protein is reacted with a coupling compound containing at least one double bond capable of copolymerization. The carrier substance is provided as a water-insoluble solid or is produced in situ by the polymerization of water-soluble monomers in the presence of the protein-coupling compound adduct. The proteins utilized in the method of this invention are typically enzymes and, of those disclosed, none contain multiple subunits.

In immunoassays (see Campbell, D. H. and Weliky, N., Methods in Immunology and Immunochemistry, Editors: Williams and Chase, Vol. 1, Academic Press, N.Y., 1967), antibodies or antigens have been passively adsorbed to surfaces, e.g., the wells of microtiter plates or plastic beads (U.S. Pat. No. 4,225,784) or to latex particles. The solid-phase antibody/polymer matrix provides a selective binding surface which, following antigen binding, can be washed to separate bound from unbound reactants.

Also known is (a) the covalent bonding of antigens or antibodies to latex beads (U.S. Pat. No. 4,181,636) or hign refractive index particles (U.S. Pat. No. 4,401,765) to measure agglutination reactions, or (b) the binding of antibodies to fluorescent polymer beads to provide specific tags for cell surface antigens (U.S. Pat. No. 4,166,105).

While the insoluble polymer/antibody materials described above provide a surface upon which selective biochemical or immunological reactions can occur, the polymers formed by bonding a molecule to an already formed polymeric material are limited in that the spacing, steric accessibility, and number of antibody molecules bound per unit length of polymer cannot be precisely or reproducibly controlled. Lot-to-lot variation is commonly encountered during the manufacture of such solid-phase polymers. In certain end-use applications where reproducibility and standardization are essential (e.g., immunoassays), the variation in composition of the solid-phase polymer/antibody material may not be acceptable.

DISCLOSURE OF INVENTION

Briefly stated, the invention discloses a method for the de novo preparation of polymers which integrally contain antibodies as part of their structure from monomer/antibody conjugates. Monomers, including polyunsaturated oligomers, or mixtures thereof, are covalently bonded directly to selected antibodies or bonded indirectly via an intermediate chemical "spacer arm" to form monomer/antibody conjugates, followed by the copolymerization of these conjugates with additional amounts of nonderivatized monomers or polyunsaturated oligomers to form copolymers that integrally contain antibodies in their structure. By controlled chemical synthesis it is possible to control the spacing, steric accessibility, number of antibody molecules contained in the polymer, specific molecular weights, densities, solubilities and physical structure of the polymeric conjugates, thus providing unique advantages for certain end-use applications. The antibody-containing polymer may be provided in the form of fibers, particles, beads, films, coatings, gels, tubes, filters, or other shaped objects, as well as porous solids, all integrally containing antibodies.

Another aspect of the invention relates to bonding of polymerizable compounds to a solid surface modified to copolymerize with the monomer/reactant conjugate during polymerization or copolymerization of the conjugate.

Another aspect of the invention relates to bonding of polymerization initiation compounds to a solid surface or to a reactant/monomer conjugate surface such that these surfaces act as initiators during the polymerization or copolymerization of the conjugate.

Another aspect of the invention relates to the selective removal of substances from solution by virtue of their ability to bind to receptors which have been conjugated to monomers. Following specific binding, the monomer/receptor conjugates are polymerized or copolymerized, whereby the specifically bound substances are removed from solution.

A further aspect of the invention is directed to the preparation of monomer/antibody conjugates for use in the methods of this invention where the antibody is covalently bonded to the unsaturated compound directly or indirectly via an intermediate chemical "spacer arm." One advantage of using spacer arms is the increased incorporation of the monomer/antibody conjugates into insoluble polymers due to the increased accessibility of the monomer to reaction with free monomers in solution.

One advantage of using, as a starting material, monomers covalently bonded to reactants such as antibodies or other receptors, is the ability to enhance the speed, sensitivity and reproducibility of separation by polymerization of the conjugate for use in immunoassay systems, affinity chromatography, and in the isolation, purification, and/or removal of chemical or biochemical substances from solutions by virtue of their capacity to bind to the antibody or receptor. Those substances that bind specifically to the antibodies or other receptors incorporated in the polymer can then be purified and/or measured. For purposes of this application, reactants are defined as substances capable of recognizing and binding to each other, typically antigens and antibodies.

Polymers integrally containing antigens or antibodies have potential biological or chemical activities and could be used for immunization. With chemically synthesized antibodies corresponding in structure to antigenic determinants, it should be possible to prepare defined polymers that can be utilized as vaccines. Alternatively, polymers integrally containing antibodies could provide biocompatible surfaces that are useful for the extracorporeal treatment of blood.

BEST MODE OF CARRYING OUT THE INVENTION

Figure 1:
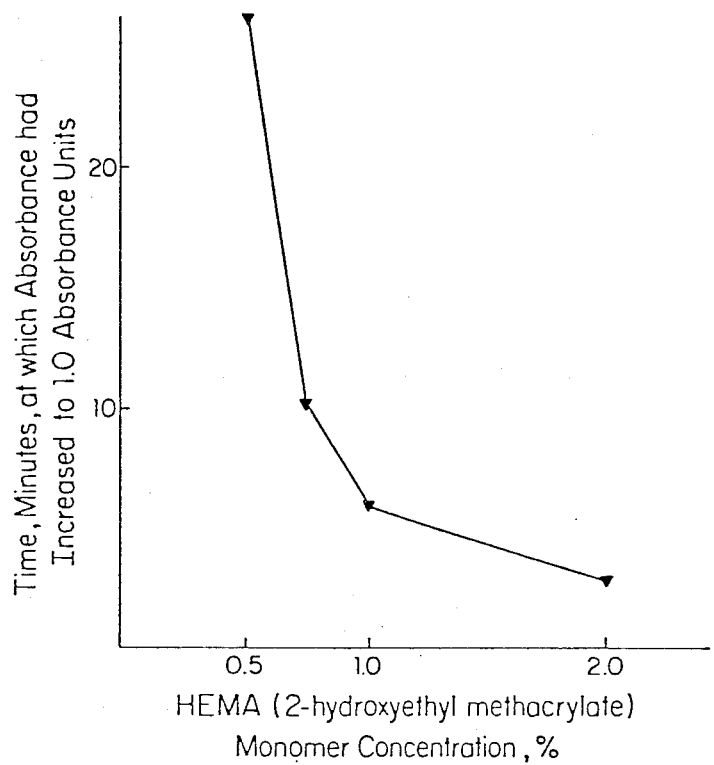
FIG. 1 depicts the effect of monomer (HEMA) concentration on the rate of formation of insoluble HEMA homopolymer particles.

This invention is carried out be first forming a monomer/antibody or monomer/reactant conjugate, then polymerizing the conjugate with itself, or copolymerizing the conjugate with predetermined amounts of nonderivatized polymerizable unsaturated compounds and/or with a polymerizable compound atached to a solid surface, to form polymers integrally containing the antibody or receptor.

The monomer/antibody conjugates are produced be covalently linking an appropriate monomer directly with a specific antibody or receptor. Alternatively, the antibody or receptor can be indirectly bonded to the monomer via an intermediate chemical compound functioning as a "spacer arm."

The antibody can be naturally occurring, the result of deliberate immunization, monoclonal or polyclonal, synthesized chemically or synthesized by using recombinant DNA (rDNA).

Receptors can include, in addition to antibodies and antigens, hormone receptors, drug receptors, lectins, transport proteins, antibody-binding proteins (e.g., Protein A), etc.

For purposes of the present invention, the term "monomer" means any polymerizable organic compound which is capable of forming covalent linkages (i.e., polymerization) under the appropriate conditions and includes certain polyunsaturated oligomers.

The term "nonderivatized polymerizable unsaturated compound" means those organic compounds capable of being polymerized under appropriate conditions and not conjugated to an antibody or other receptor.

The term "integrally containing" means that the antibody or receptor is covalently bonded to a component of the polymer directly or indirectly prior to, or as the polymer is being formed, rather than being coupled to a preformed polymer.

Monomers which can be used include ethylenic or acetylenic unsaturation and at least one reactive site for binding to a corresponding reactive site on the antibody or to an intermediate chemical compound functioning as a "spacer arm." Such compounds may include:

(a) molecules containing olefinic unsaturated groups and at least one reactive site for bonding with the antibody, receptor or "spacer arm" compound, e.g.:

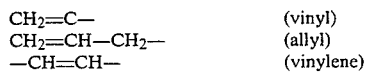

(b) molecules having acetylenic unsaturation and at least one reactive site for bonding with the antibody, receptor or spacer compound; and (c) polyunsaturated molecules, such as monomers containing olefinic unsaturation and having at least one reactive site for bonding with the antibody, receptor or spacer compound, e.g.:

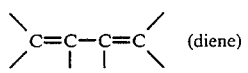 (diene)

Monomers which may be used include:

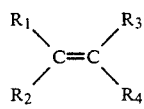

where $R_1$ and $R_3$ = H or —$CH_3$
$R_2$ = H, $CH_3$, or —CH=$CH_2$
$R_4$ = —COCl
—CN
—OH
—COOH
—COOR$_6$ where R$_6$ = an alkyl radical having from 1-6 carbon atoms

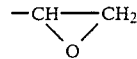

$$-\overset{O}{\underset{\|}{C}}-O(C_nH_{2n})OH \text{ where n = 2 to 4}$$

—NH$_2$
—NHR$_6$ where R$_6$ = an alkyl radical having from 1-6 carbon atoms
—NCO
—CONH$_2$
—CONHR$_6$ where R$_6$ is defined as above
—CONHCH$_2$OH
—CH$_2$NH$_2$
—CH$_2$Cl
—CO$_2$(C$_n$H$_{2n}$)NH$_2$ where n = 2 to 4
—CO$_2$(C$_n$H$_{2n}$)NHR$_6$

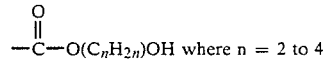

—CO$_2$CH$_2$—CH—CH$_2$OH
    |
    OH

—CHO

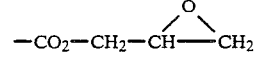

—CO$_2$(CH$_2$)$_n$NCO where n = 1 to 4

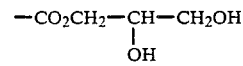

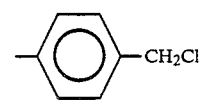

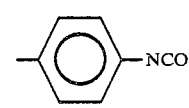

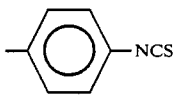

Specific monomers which can be used include acrylic or methacrylic acid, acrylonitrile or methacrylonitrile, acryloyl or methacryloyl chloride, glycidyl acrylate or methacrylate, glycerol acrylate or methacrylate, allylamine, allyl chloride; hydroxy-lower-alkyl-acrylates, such as 2-hydroxyethyl methacrylate or 3-hydroxypropyl methacrylate, and amino-lower-alkylacrylates, such as 2-amino-ethyl methacrylate. Preferred are monomers which are soluble in water or water/polar organic solvent mixtures.

Polymerizable polyunsatured oligomers which may be used with or in lieu of the compounds previously described include those containing one or more olefinic groups and at least one reactive site for bonding to an antibody, a receptor, or an intermediate chemical "spacer arm" compound. The reactive sites may include the functionalities previously referenced with regard to the monomers. Oligomers of the type which may be used include:

(i) Molecules with pendant unsaturation and reactable pendant and terminal groups;

Molecules with pendant and terminal unsaturation and reactable pendant groups;

Molecules with both pendant reactable and unsaturated groups;

Molecules with pendant unsaturated groups and reactable terminal groups;

(ii) Molecules with main chain unsaturation and reactable terminal groups;

(iii) Molecules with main chain unsaturation and one reactable terminal group; and

Molecules with one unsaturated terminal group and one reactable terminal group.

where —O = a reactive polar group and "=" = unsaturation

The reactive sites on the antibody or receptor may include, for example, covalently bondable functionalities such as hydroxyl, amine, carboxyl or sulfhydryl groups.

Covalent bonding of the monomer to the antibody, receptor, or its attached carbohydrate (in the case of glycoproteins) may be carried out by known chemical methods. For example, the monomer and/or the antibldy or receptor can be activated to produce a stable but reactive intermediate which can be subsequently coupled. The antibody or receptor may also be activated, for example, by periodate oxidation of the attached carbohydrates if the antibody is glycosylated. This reaction forms aldehydes which can then condense with amino groups on the monomer, such as 2-aminoethyl methacrylate, to form a Schiff base. This Schiff base can be reduced with sodium borohydride to form a stable covalent linkage. The monomer in the form of an acid halide or anhydride may also be directly reacted with the antibody in the presence of an acid scavenger to remove acid as it is formed during the reaction. Bifunctional or hetero-bifunctional coupling reagents may also be used. Such bifunctional or hetero-bifunctional reagents are well known. The bifunctional and/or hetero-bifunctional reagents may be biodegradable, if desired, permitting release of the antibody or receptor over an extended period of time. In almost all cases, the reaction conditions, i.e., time, temperature, solvent, and pH, should be such as to avoid denaturation and/or degradation of the antibody or receptor.

A further aspect of this invention relates to the chemical bonding of the monomer to a chemical. intermediate compound which acts as a "spacer arm," the antibody or receptor also being bonded to the chemical intermediate compound. The "spacer arm" provides greater accessibility of the antibody or receptor portion of the conjugate to substances to which it can bind for removal or extraction of those substances from a solution. Chemical intermediate compounds which may be used include bifunctional compounds having a reactive site for bonding with the monomer and a reactive site for bonding to the antibody. Reactive sites may include, for example, functional groups such as —OH, —COOH or —NH$_2$. Examples of chemical intermediate compounds which may be used include, R—(CH$_2$)$_n$—R where n=2 to 10 and R is —OH, —NH$_2$, or —COOH, such as ε—amino caproic acid, 1,4-diaminobutane, hexamethylenediamine, 1,4-butanediol and similar compounds.

Homopolymerization of the monomer/antibody or monomer/receptor conjugate with itself or copolymerization with nonderivatized polymerizable compounds can be carried out by generation of free radicals using chemical, radiation (light, ultraviolet, gamma or beta), and/or thermal means. Many antibodies are unstable to heat and many are sensitive to radiation. Nonderivatized polymerizable compounds which may be used include those previously discussed, for example, monomers, such as alkyl acrylates or methacrylates where the alkyl radical contains from 1 to 8 carbons, acrylonitrile and vinyl acetate; and polyunsaturated monomers or oligomers previously discussed. Also, cross-linking compounds may be copolymerized with the monomer/antibody or monomer/receptor conjugate. Such cross-linking compounds may include, for example, N,N'-methylenebisacrylamide, or a di-, tri- or tetramethacrylates or acrylates.

The relative amounts of the monomer/antibody or monomer/receptor conjugate and nonderivatized polymerizable compound employed, the composition and concentration of the unsaturated compound, temperature, solvent, pH, and the particular initiator system utilized allow the specific molecular engineering of an antibody-containing or receptor-containing polymer having desired properties. The percentage of derivatized to nonderivatized compound in the polymer may vary from traces up to 100%, but the preferable range is between 0.001 to 100% derivatized compound and 0 to 99.999% nonderivatized compound.

The monomer/reactant conjugate, rather than being copolymerized only with nonderivatized polymerizable compounds, may also be reacted with solid surfaces where the surface has been chemically modified to render it reactable with pendant groups attached to a polymerizable compound. Such solid surfaces may be in the form of microbeads, membranes, fibers, porous solids etc. For immunoassay purposes, for example, a polymerizable compound is bonded to a solid surface. The monomer/reactant is incubated with an analyte and a reporter provided for labeling the monomer/reactant conjugate—analyte complex. During copolymerization of the conjugate with the polymerizable compound bonded to the solid surface, the concentration of the reporter at the surface of the solid is enhanced, resulting in a more rapid and sensitive assay. The solid surface may be a polysaccharide, hydrocarbon polymer, fluorocarbon polymer, polyamide, polyurethane, polyester, vinyl polymer, cellulosic polymer or derivative of a cellulosic polymer, glass, silicone polymer.

There are numerous methods by which a polymerizable compound may be attached to a solid polymeric surface.

(a) Solid polymeric surfaces containing aromatic groups such as polystyrene or polyethylene teraphthalate, may be treated to render the surface of the solid polymeric surface reactive with pendant groups contained on a monomer. For example, polystyrene microbeads may be reacted with chlorosulfonic acid to yield the corresponding aromatic sulfonyl chlorides which can then be reacted with a pendant amide group attached to a vinyl monomer or with a alkyldiamine to yield a corresponding compound having pendant primary amine groups which are reactive with pendant groups attached to a vinyl monomer having a pendant carboxylic acid conjugate with N-hydroxy succinimide or a pendant acid chloride.

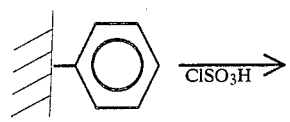

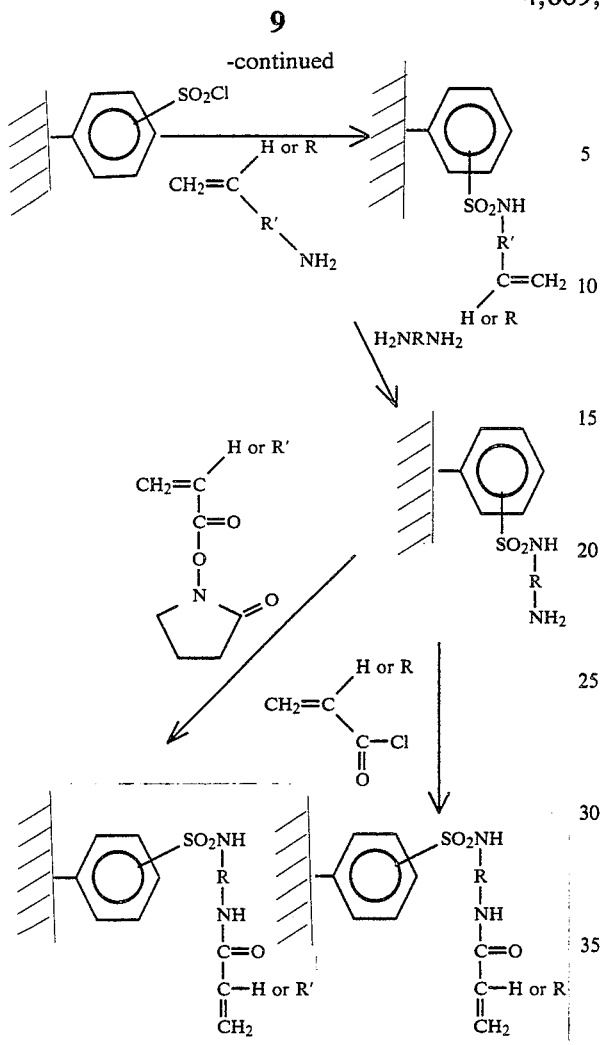

where R and R'=alkyl radicals having from 1 to 8 carbon atoms.

(b) Glass surfaces or siliconized surfaces of solids as silicone polymers in whatever form desired i.e., microbead, fiber etc., may be chemically treated to provide surfaces reactive with pendant groups attached to polymerizable compounds, as for example:

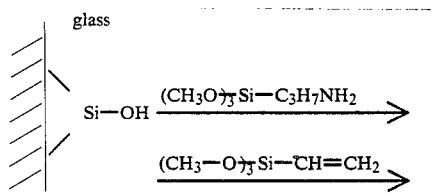

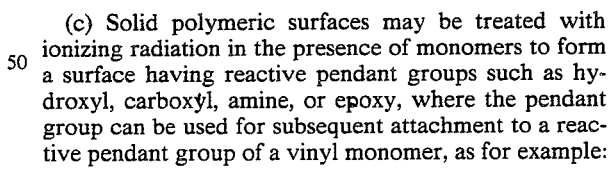

React (3) or (5) above with:

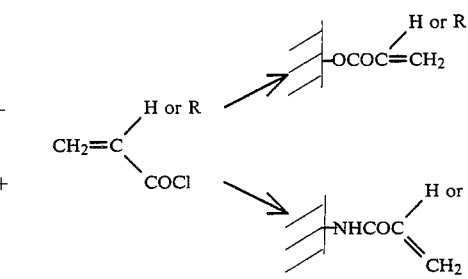

(c) Solid polymeric surfaces may be treated with ionizing radiation in the presence of monomers to form a surface having reactive pendant groups such as hydroxyl, carboxyl, amine, or epoxy, where the pendant group can be used for subsequent attachment to a reactive pendant group of a vinyl monomer, as for example:

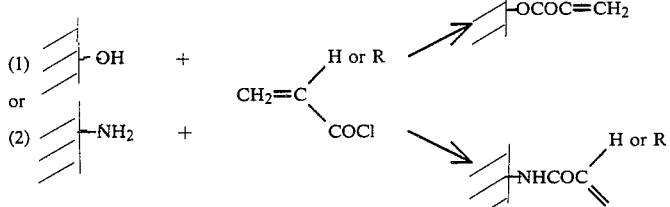

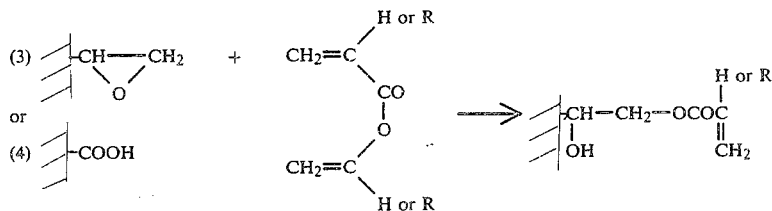

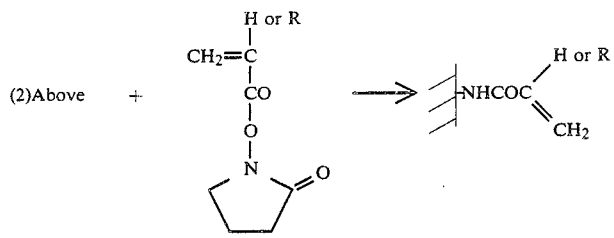

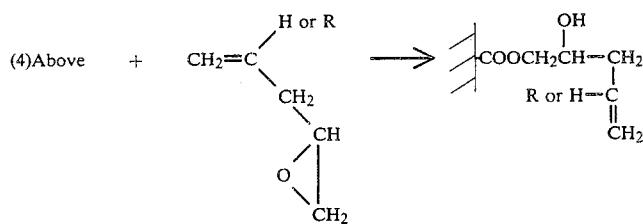

(d) Rather than create reactive sites on the polymeric surface, initiation sites for free radical polymerization may be created with oxidizing agents by a number of known methods, including:

1. creation of hydroperoxide and/or peroxide sites on the solid surface by: (a) reaction of the surface with air or oxygen in the presence of ionizing radiation from a radioactive source such as $Co^{60}$ or ultraviolet radiation; (b) subjecting the surface to plasma discharge in the presence of oxygen; or (c) thermally treating the surface in the presence of air, oxygen or ozone. The resulting modified surface is then subjected to heat and/or a reducing agent to form active initiation sites on the solid polymeric surface which are subsequently reacted with vinyl monomer/reactant conjugates and other polymerizable compounds.

2. creation of photosensitive initiation sites on solids or polymeric or protein surfaces by: (a) reacting solid surfaces having pendant reactive groups, such as amine, hydroxyl sulfhydryl or epoxy groups, to yield a surface which can be reacted with a monomer/reactant conjugate; or

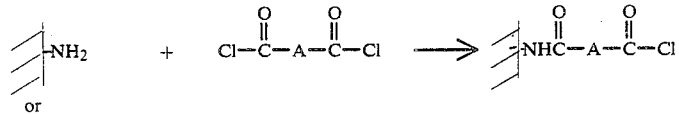

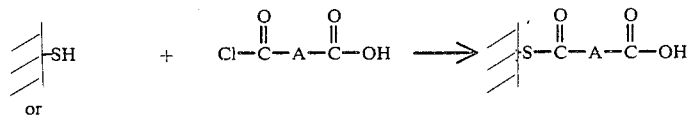

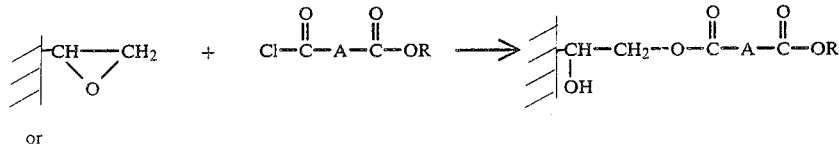

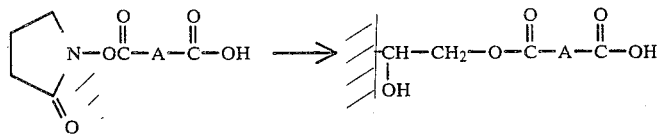

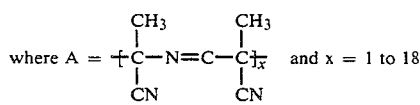

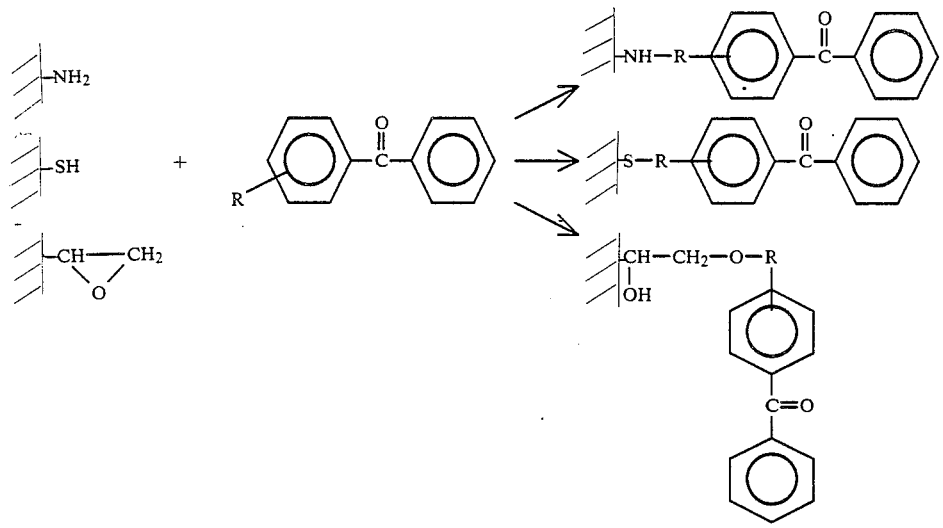

3. forming radiation graft copolymers using a monomer incorporating a photosensitizer, as for example,

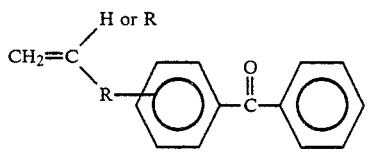

Free-radical polymerizations may be conducted around room temperature (25° C.) with or without agitation. A surface active agent may or may not be present. Although the reaction may be carried out in the presence of oxygen, it is generally preferred to conduct the reaction in the absence of oxygen or in the presence of a controlled amount of oxygen. The pH range may vary widely from pH 3 to pH 10, although it is preferable to select a pH where the antibody or receptor remains the most stable, which is typically between pH 6 and pH 8 for most antibodies. If a surface active agent is used, suitable compounds, such as sodium dodecyl sulfate, sodium stearate, or nonionic materials, such as polyethylene oxide lauryl ether, may be employed.

The free radicals may be generated by "redox" or oxidation-reduction initiation, light or photochemical initiation, ionizing radiation initiation, or thermal initiation. An advantage of oxidation-reduction initiation, light or photochemical initiation, and ionizing radiation initiation is production of free radicals at reasonable rates at relatively low temperatures, such as ambient or body temperature. Types of oxidation-reduction initiators which may be used include (1) peroxides in combination with a reducing agent, e.g., hydrogen peroxide with ferrous ion, or benzoyl peroxide with an N,N-dialkylaniline or toluidine, and (2) persulfates in combination with N,N,N',N'-tetraethylmethylenediamine (TEMED) or a reducing agent, such as sodium metabisulfite or sodium thiosulfate. Specifically, ammonium persulfate, benzoyl peroxide, lauryl peroxide, t-butyl hydroperoxide, t-butyl perbenzoate, cumene hydroperoxide, or mixtures thereof with TEMED or reducing agents, such as sodium bisulfite or sodium thiosulfate, may be used. It also appears that sodium bisulfite alone may be used for polymerization.

Photoinitiated polymerization may also be used by employing a photoinitiator, such as azodiisobutyronitrile or azodiisobutyroamide, benzoin methyl ether, riboflavin, thiazine dyes, such as methylene blue or eosin, and transition metals, such as ferric chloride or diazidotetramminecobalt (III) azide, in combination with ultraviolet and/or visible light irradiation of the reaction system.

Ionizing radiation may also be employed utilizing radiation from a radioactive source or a particle accelerator.

Polymerization may be carried out in the presence of various physiological materials, such as proteins, and under various physiological conditions, such as neutral pH in isotonic buffered saline solution.

Monomer covalently bonded to a receptor to form a monomer/receptor conjugate capable of binding to other substances after preparation, can also be employed in an aqueous solution or suspension thereof for selectively removing a compound from the solution or suspension for purposes of analysis, isolation or purification. The conjugate is incubated in the solution or suspension for an appropriate period of time to effect specific binding between the receptor and the cognate compound in the solution or suspension. Polymerization of the conjugate is then initiated to effect separation of the conjugate from the remainder of the materials in the solution or suspension.

Examples presented utilize a representative monomer (2-hydroxyethyl methacrylate, HEMA) and a representative antibody (mouse monoclonal antibody 2H1, MAb, which reacts with the kappa chain of human IgG). To summarize the examples which follow, Example I demonstrates the polymerization of HEMA monomer in a buffered saline solution. In order to assure noninterference in this polymerization process by "bystander" polypeptides, this reaction was also conducted in the presence of a mixture of normal serum proteins. Example II demonstrates a method of producing an activated form of an acrylic acid monomer which is to be conjugated to the MAb, Example III demonstrates the covalent conjugation of the activated acrylic acid monomer to the MAb, to form the monomer/antibody conjugate. To monitor the amount of acrylic acid monomer covalently bound to the MAb the amount of free acrylic monomer in solution before and after the conjugation reaction was determined. Gel separation by isoelectric focusing of MAb heavy and light chains also demonstrated binding of the acrylic monomer to the antibody. Example IV demonstrates copolymerization of the monomer/MAb, conjugate (MAb/M) with additional nonderivatized HEMA monomer, resulting in synthetic polymer particles that integrally contain MAb in their structure. For the purpose of demonstration, the MAb/M conjugate was first fluorescently tagged with fluorescein isothiocyanate. Polymer particles containing these fluorescein-tagged MAb/M molecules were then visualized under the fluorescence microscope. Additionally, the fluorescence of individual polymer particles was quantitated by flow analysis using a flow cytometer.

EXAMPLE I

POLYMERIZATION OF HEMA MONOMER IN A BUFFERED SALINE SOLUTION

Polymerization of 2-hydroxethyl methacrylate in the presence of physiological compounds was carried out as follows: to 2.73 mL of distilled water or phosphate buffered saline, pH 7.4, was added 0.06 to 0.24 mL of 25% (v/v) 2-hydroxyethyl methacrylate (HEMA, Aldrich Chemical Company). Water was added to a final volume of 2.97 mL, as necessary. After bubbling prepurified nitrogen through a Pasteur pipette into the bottom of the cuvet for at least five minutes, 30 microliters of 1M $Na_2S_2O_5$ was added and the precipitation of the resulting polymer was followed at 550 nm with a Beckman Model 26. From this data, a concentration of 2% was chosen.

Inclusion of fetal calf serum, up to 10% (v/v), or "Nonidet P-40", a nonionic detergent, at concentrations up to 1% (w/v), had no effect on the rate of formation of the polymer particles. Since fetal calf serum contains a variety of proteins and other physiological compounds, this indicates that most proteins and physiological compounds will not inhibit formation of the polymer particles. Since nonionic detergents are commonly used in immunoassays to solubilize biological substances, this indicates that it will be possible to utilize detergents in polymerizationinduced separation immunoassays without interference.

EXAMPLE II

SYNTHESIS OF AN ACTIVATED ACRYLIC ACID MONOMER FOR COUPLING TO ANTIBODY

A mixture containing N-hydroxysuccinimide (NHS) (4.6 g, 40 mmol) and acryloyl chloride (18 mL, 220 mmol) was refluxed with vigorous stirring for 3 hours in an anhydrous atmosphere and the reaction mixture, a homogeneous solution, was evaporated to a syrup. Distilled water (50 mL) was added to the syrup and the mixture was stirred for 30 minutes at 4° C. Upon addition of chloroform (50 mL), the mixture was separated into layers, and the organic layer was extracted successively with water (50 mL each time, 5 times usually) until the pH of the water layer was approximately 5. The aqueous solutions so obtained were combined and extracted once with chloroform (50 mL); this chloroform solution and the chloroform solution from above were combined, dried over sodium sulfate, and evaporated to a syrup. Crystals, obtained by storing the syrup overnight at −20° C., were triturated with diethyl ether, and harvested by filtration.

Recrystallization from absolute ethanol yielded 2.0 g of the desired product. This compound was analyzed by mass spectrometry, infrared spectroscopy, NMR, liquid chromatography, and melting point, and proved to be the N-hydroxysuccinimide ester of acrylic acid.

EXAMPLE III

PREPARATION AND CHARACTERIZATION OF A MONOMER/ANTIBODY CONJUGATE

The N-hydroxysuccinimide ester of acrylic acid (NSA) was reacted with mouse monoclonal antibody (MAb) 2H1 as follows: 2.2 mg MAb in 0.29M sodium carbonate buffer, pH 9.3, was added to 20 micrograms of NSA in a total volume of 0.5 mL. The reaction mixture was incubated at 37° C. for one hour with constant stirring. Of this solution, 100 microliters was then taken for an analysis by reversedphase high-performance liquid chromatography (RP-HPLC), which revealed the amount of free acrylic acid (arising from nonspecific hydrolysis of NSA) and remaining MSA in the reaction mix (Table 1).

TABLE 1

| RESULTS OF HPLC ANALYSIS OF MONOMER CONJUGATION REACTION MIXTURE | | | |
|---|---|---|---|
| | Antibody | NSA (Activated monomer) | Monomer (Acrylic acid) |
| Amount added, nanomoles | 14.5 | 116.0 | 0.0 |
| Amount detected in solution, monomers | Not determined | 0.0 | 26.7 |

This indicated that a net of 89 nanomoles of monomer was attached to the 14.5 nanomoles of MAb for a ratio of 6.2 monomer molecules per MAb.

To remove residual NSA and its hydrolysis products and for further characterization of the derivatized antibody, 200 microliters of the reaction mixture was chromatographed on a column of Sephadex ® G-25 (beads of dextran cross-linked with epichlorohydrin from Pharmacia Fine Chemicals AB, Uppsala, Sweden) in the same carbonate buffer to which bovine serum albumin, 0.1 mg/mL, was added to prevent nonspecific adsorption of polypeptides to the Sephadex ® G-25.

To show that the purified monomer/antibody conjugate was still active, it was tested in an enzyme-linked immunosorbent assay (ELISA), and the results indicated no loss of antigen binding capacity. For this purpose, the antigen (human IgG, which contains kappa light chains) was adsorbed to the surfaces of wells in a micro ELISA plate (96 wells). The wells were washed, residual nonspecific adsorbing sites on the plastic surface were blocked with bovine serum albumin, and then the wells were incubated with serial dilutions of the antibodies (control nonconjugated antibody or monomer/antibody conjugate). The plate was again washed, incubated with goat anti-mouse immunoglobulin conugated to horseradish peroxidase (Tago, Inc., Burlingame, Calif. 94010), washed, and incubated with the substrates for horseradish peroxidase, o-phenylenediamine and hydrogen peroxide. Dilute aqueous sulfuric acid was added to stop the reaction, the plates were assayed on a micro ELISA reader, and the optical densities of each dilution of monomer/antibody conjugate compared with that of the control antibody. On a molar basis, the monomer/antibody conjugate demonstrated comparable activity to the nonconjugated antibody.

A sample of the monomer/antibody conjugate was then analyzed by isoelectric focusing. In this procedure, the polypeptide subunits of the proteins were separated according to their isoelectric point, or pH at which they had no net positive or negative charge. For this purpose, the heavy and light chains of the monomer/antibody conjugate were first dissociated in the presence of 3% (w/v) sodium dodecyl-sulfate (SDS) and 5% (v/v) 2-mercaptoethanol and separated on the basis of molecular weight by electrophoresis in an SDS-polyacrylamide slab gel. The separated heavy and light chains were cut out from the gel and analyzed further by isoelectric focusing in a polyacrylamide slab gel according to their isoelectric point. Staining of the isoelectric focusing gel with dye (Coomassie Brilliant Blue R-250) provided a characteristic pattern of bands for each sample. Since both the heavy and light chains of antibodies are glycoproteins which contain intrinsic variations in their sialic acid content, each heavy and light chain can be separated be charge into a characteristic family of bands, the different bands being comprised of polypeptides having differing amounts of sialic acid. As the reaction of the activated acrylic acid occurred primarily with amino functional groups on protein lysine residues, the addition of monomer to MAb would be expected to neutralize one positive charge on the protein submit for each molecule of acrylic acid attached. This in turn would be expected to change the isoelectric point of the derivatized protein.

Figure 2:
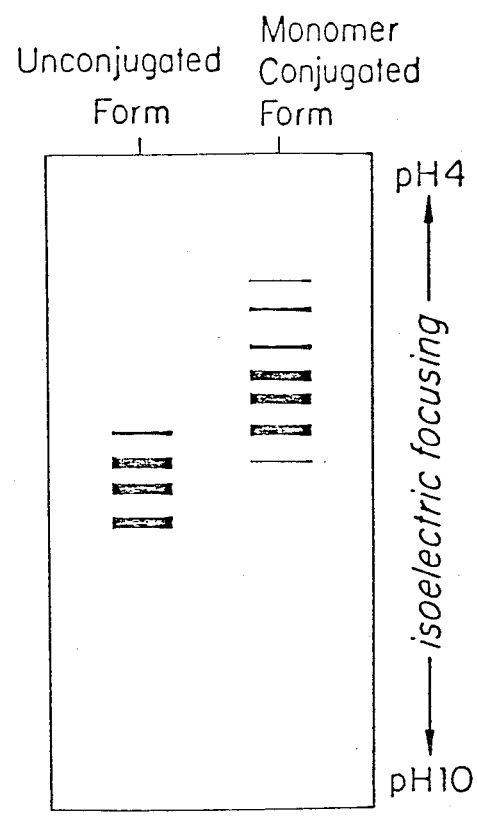
FIG. 2 is a diagrammatic representation of a polyacrylamide isoelectric focusing gel of the heavy chain of antibody 2Hl before and after conjugation with acrylic acid.
Figure 3:
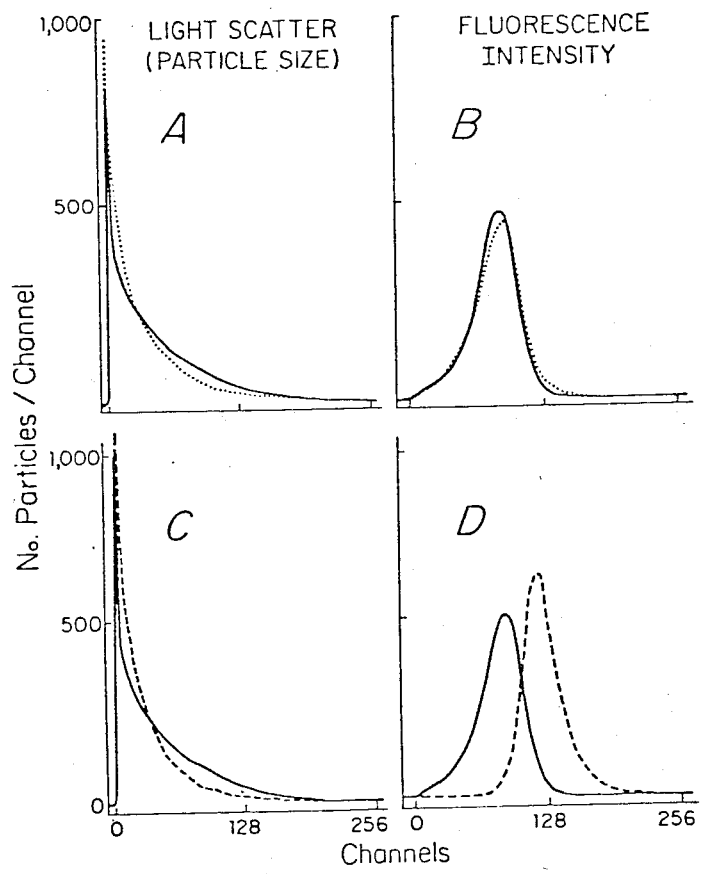
FIG. 3 depicts the incorporation of fluoresceintagged monomer/antibody conjugates into insoluble antibody-containing polymer particles.

The results of the isoelectric focusing analysis indicated that each heavy chain was modified be the covalent attachment of approximately three acrylic acid monomers (FIG. 2). Analysis also indicated that the electrophoretic pattern of monomer-derivatized light chain was so close to the nonderivatized polypeptide pattern that essentially minimal conjugation of monomer to light chains had occurred. On this basis, it was estimated that six moles of acrylic acid monomer was conjugated to each mole of antibody (3 per heavy chain times 2 heavy chains per antibody), which was in agreement with the analysis be RP-HPLC.

EXAMPLE IV

DEMONSTRATION OF INCORPORATION OF MONOMER/ANTIBODY CONJUGATE INTO POLYMER

In order to provide a means of identifying and monitoring the presence of antibody molecules in polymers, the monomer/antibody conjugate (MAb/M) was covalently tagged with a fluorescent compound. For this purpose, 88 micrograms (8.8 microliters of 10 mg/mL in DMSO) of fluorescein isothiocyanate isomer II (FITC) was added to 3.6 mg MAb/M in 1.2 mL of 0.29M carbonate buffer, pH 9.3. The mixture was stirred for 1 hour at 37° C. and chromatographed on a column of Sephadex ® G-25 in phosphate-buffered saline to which bovine serum albumin (0.01 mg/mL) had been added to prevent nonspecific adsorption to the column. This separated the fluorescein-tagged MAb/M from any free fluorescein isothiocyanate that remained in solution.

The fluorescein-tagged MAb/M conjugates were then copolymerized with additional HEMA to form insoluble polymer particles. Two methods were used to demonstrate the incorporation of the fluorescein-tagged MAb/M into the de novo synthesized polymer. Both methods, fluorescence microscopy and quantitative analysis by flow cytometer, actually measured the presence of fluorescence in the polymer particles. For comparison, two controls were used (samples a and be. In sample a, HEMA was polymerized by itself into insoluble polymer particles in a smaller version of the polymerization system of Example I (total volume: 1 mL). In sample b, 50 micrograms of a fluorescein-tagged (but not monomer-conjugated) "bystander" MAb, was added to the polymerization system to test for nonspecific entrapment of bystander antibodies during the formation of insoluble polymer particles. In neither case was any fluorescence seen to be associated with the polymer particles when viewed in the fluorescence microscope. In sample c, 50 micrograms of monomer-conjugated, fluorescein-tagged MAb/M was added to the polymerization system to test for specific incorporation of the antibody, via copolymerization, into the polymer particles. In this case, all of the fluorescence was seen to be associated with the polymer particles when viewed in the fluorescence microscope.

The same experiment was examined quantitatively with a flow cytometer. After the polymerization had proceeded for ten minutes, the suspension of polymer particles was diluted one-hundred-fold and then introduced into a flow cytometer (Becton Dickinson, FACS IV) equipped with an Argon ion laser light source. In this procedure, the suspended particles were carried single-file in a laminar stream of buffer. Interrogation of the particle stream with the laser beam generated light scatter each time a particle entered the laser pathway. The extent of the light scatter was a reflection of particle size and shape. Further, measurement of light scatter can also be used to electronically trigger a simultaneous measure of fluorescence emitted from the particle. In this way, fluorescence specifically associated with polymer particles can be selectively measured.

The results can be summarized as follows:

Light Scatter Analysis

Light scatter analysis panels A and C) of polymer particles formed with HEMA alone (solid line), polymer particles formed from HEMA polymerized in the presence of bustander antibody (dotted line), and polymer particles formed by copolymerization of HEMA with fluorescein-tagged MAb (dashed line), shows that the particle size distribution was substantially the same for all three samples.

Fluorescence Analysis.

Panel B compares the fluorescence intensity of polymer particles formed from HEMA alone (solid line) and polymer particles formed from HEMA polymerized in the presence of bystander antibody (dotted line). The fluorescence intensity was substantially the same for both samples. Since the intensity was substantially the same regardless of whether or not fluorescein-tagged bystander antibody was present, the weak fluorescence signal of both samples was assumed to be due to autofluorescence of the HEMA polymer itself and indicated that there was minimal nonspecific entrapment of the bystander antibody in the polymer. Panel D compares the fluorescence intensity of polymer particles formed from HEMA alone (solid line) and those formed be copolymerization of HEMA with the monomer-derivatized, fluorescein-tagged MAb (dotted line). The fluorescence intensity of the copolymer particles formed be copolymerization of monomer-derivatized, fluorescein-tagged MAb and HEMA was shifted over 28 channels relative to the control. The fluorescence intensity scale (x axis) is logarithmic, and a shift of 28 channels corresponded to a three-fold increase in fluorescence intensity. This dramatic increase in the fluorescence intensity provided conclusive evidence that the monomer-derivatized, fluorescein-tagged MAb was integrally incorporated into the polymer particles.

From the foregoing, it will be appreciated that, although specific embodiments of the invention have been described herein for purposes of illustration, various modifications may be made without deviating from the spirit and scope of the invention. Accordingly, the invention is not limited except as by the appended claims.

We claim:

1. A method for the de novo synthesis of antibody-containing polymers, comprising:
    forming a monomer/antibody conjugate with the antibody covalently bonded to the monomer, and
    initiating polymerization of the monomer/antibody conjugate to form polymers integrally containing the antibody.

2. The method of claim 1 wherein the monomer is bonded to a chemical intermediate "spacer arm" compound which is also bonded to the antibody.

3. The method of claims 1 or 2 wherein polymerization is initiated with nonderivatized polymerizable compounds to form copolymers integrally containing the antibody.

4. The method of claim 1 wherein the antibody is selected from the group consisting of naturally occurring, monoclonal, polyclonal, chemically synthesized and recombinant DNA (rDNA)-derived.

5. The method of claim 1 wherein the monomer/antibody conjugate is soluble in water or water/polar organic solvent mixtures.

6. The method of claims 1 or 2 wherein the monomer is a compound containing olefinic or acetylenic unsaturation and at least one reactive site for bonding with the antibody or intermediate "spacer arm" compound.

7. The method of claims 1 or 2 wherein the monomer is a polyunsaturated, polymerizable oligomer having at least one reactive site for bonding with the antibody or intermediate "spacer arm" compound.

8. The method of claim 3 wherein the nonderivatized polymerizable compounds are selected from the group consisting of olefinically unsaturated compounds, acetylenically unsaturated compounds, polyunsaturated compounds and multi-functional cross-linking compounds, 9. A conjugate used in the de novo preparation of polymers containing one or more antibodies, comprising:
    a monomer containing at least one reactive site for bonding with an antibody; and
    an antibody convalently bonded thereto.

10. The conjugate of claim 9 wherein the antibody is selected from the group consisting of naturally occurring monoclonal, polyclonal, chemically synthesized and recombinant DNA (rDNA)-derived.

11. The conjugate of claim 9 wherein the antibody is bonded to an intermediate "spacer arm" compound which is also bonded to the monomer.

12. The conjugate of claim 9 wherein the monomer is soluble in water or water/polar organic solvent mixtures.

13. The conjugate of claims 9 or 11 homopolymerized to form a polymer integrally containing the antibody.

14. The polymer or copolymer of claim 13 wherein the polymer is soluble in water or water/polar organic solvent mixtures, and capable of being formed into shaped solids, films, particles, tubes, fibers, coatings, gels, and filters, upon removal of the water.

15. The polymer or copolymer of claim 13 wherein the polymer is water-insoluble and capable of being formed into shaped solids, films, particles, tubes, fibers, coatings, gels and filters.

16. The conjugate of claims 9 or 11 copolymerized with nonderivatized monomer to form a copolymer integrally containing the antibody.

17. The conjugate of claims 9 or 11 wherein the monomer is a compound containing olefinic or acetylenic unsaturation and at least one reactive site for bonding with the antibody or intermediate "spacer arm" compound.

18. The polymer or copolymer of claim 16 wherein the polymer is soluble in water or water/polar organic solvent mixtures, and capable of being formed into shaped solids, films, particles, tubes, fibers, coatings, gels, and filters, upon removal of the water.

19. The polymer or copolymer of claim 16 wherein the polymer is water-insoluble and capable of being formed into shaped solids, films, particles, tubes, fibers, coatings, gels and filters.

20. The conjugate of claims 9 or 11 wherein the monomer is a polyunsaturated oligomer having at least one reactive site for bonding with the antibody or intermediate "spacer arm" compound.

21. The conjugate of claim 16 wherein the nonderivatized compound is selected from the group consisting of olefinically unsaturated compounds, acetylenically unsaturated compounds, polyunsaturated compounds and multi-functional cross-linking compounds.

22. The conjugate of claims 9 or 11 wherein the monomer is one selected from the group consisting of:

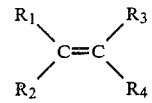

where $R_1$ and $R_3$ = H or $-CH_3$
$R_2$ = H, $-CH_3$, or $-CH=CH_2$
$R_4$ = $-COCl$
    $-CN$
    $-OH$
    $-COOH$
    $-COOR_6$ where $R_6$ = alkyl radicals having from 1–6 carbon atoms

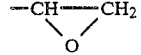

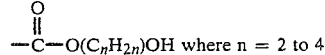

$-C-O(C_nH_{2n})OH$ where n = 2 to 4

$-NH_2$

-continued

—NHR$_6$ where R$_6$ = alkyl radicals having from 1–6 carbon atoms

—NCO

—CONH$_2$

—CONHR$_6$ where R$_6$ is as defined above

—CONHCH$_2$OH

—CH$_2$NH$_2$

—CH$_2$Cl

—CO$_2$(C$_n$H$_{2n}$)NH$_2$ where n = 2 to 4

—CO$_2$(C$_n$H$_{2n}$)NHR$_6$

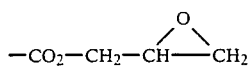

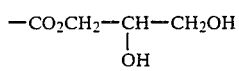

—CHO

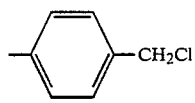

—CO$_2$(CH$_2$)$_n$NCO where n = 1 to 4

-continued

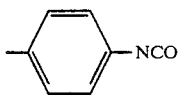

23. A method of selectively binding a compound for removal from a solution or suspension containing the compound, comprising:
providing a monomer/reactant conjugate;
providing a solid surface having at least one polymerizable compound bonded thereto capable of copolymerizing with the monomer/reactant conjugate;
contacting the compound to be removed with the monomer/reactant conjugate to bind the compound to the reactant and form a monomer/reactant—compound complex; and
polymerizing the monomer in the presence of the polymerizable compound bonded to the solid surface.

24. The method of claim 23 wherein the polymerizable compound is bonded to the solid surface by chemically modifying the surface to render it reactable with pendant groups attached to the polymerizable compound.

25. The method of claim 24 wherein the solid surface includes aromatic groups reactive with pendant groups attached to a vinyl monomer.

26. The method of claim 24, including creating initiation sites on the solid surface from free radical polymerization.

* * * * *